| United States Patent [19] | [11] Patent Number: 4,978,765 |
| Sasaki et al. | [45] Date of Patent: * Dec. 18, 1990 |

[54] PROCESS FOR THE PRODUCTION OF ACRYLONITRILE

[75] Inventors: Yutaka Sasaki; Kunio Mori; Kiyoshi Moriya, all of Kanagawa, Japan

[73] Assignee: Nitto Chemical Industry Co., Ltd, Tokyo, Japan

[*] Notice: The portion of the term of this patent subsequent to Oct. 23, 2007 has been disclaimed.

[21] Appl. No.: 337,803

[22] Filed: Apr. 14, 1989

[30] Foreign Application Priority Data

Apr. 15, 1988 [JP] Japan .................................. 63-91698

[51] Int. Cl.$^5$ ............................................. C07C 253/26
[52] U.S. Cl. ...................................................... 558/324
[58] Field of Search ......................................... 558/324

[56] References Cited

U.S. PATENT DOCUMENTS

| 4,139,552 | 2/1979 | Grasselli et al. | 558/324 |
| 4,212,766 | 7/1980 | Brazdil et al. | 558/324 X |
| 4,323,520 | 4/1982 | Hardman et al. | 558/324 X |
| 4,495,109 | 1/1985 | Grasselli et al. | 558/324 |
| 4,659,689 | 4/1987 | Suresh et al. | 558/324 X |
| 4,766,232 | 8/1988 | Grasselli et al | 558/324 |

*Primary Examiner*—Joseph P. Brust
*Attorney, Agent, or Firm*—Sughrue, Mion, Zinn, Macpeak & Seas

[57] ABSTRACT

A process for the production of acrylonitrile by vapor phase catalytic ammoxidation of propylene in a fluidized bed at high yield with the use of a multicompenent fluidized bed catalyst comprising molybdenum, bismuth, iron, antimony, nickel and alkali metal(s) each carried by silica, which has a high catalytic activity and a high attrition resistance and which does not require any expensive cobalt catalytic component.

8 Claims, 1 Drawing Sheet

PROCESS FOR THE PRODUCTION OF ACRYLONITRILE

FIELD OF THE INVENTION

This invention relates to a process for the production of acrylonitrile by vapor phase catalytic ammoxidation in a fluidized bed. More particularly, it relates to a process for the production of acrylonitrile by the vapor phase catalytic ammoxidation of propylene in a fluidized bed with the use of a molybdenum/bismuth/ iron-/antimony/nickel/alkali metal(s) catalyst which is capable of providing a high acrylonitrile yield and has a high mechanical strength.

BACKGROUND OF THE INVENTION

A number of catalysts have been proposed for the production of acrylonitrile by the ammoxidation of propylene. Particularly, various multi-component molybdenum/bismuth catalysts are used as these catalysts. Examples of these processes include those disclosed by JP-B-36-5870 (U.S. Pat. No. 2,904,580) (the term "JP-B" as used herein means an "examined Japanese patent publication"), JP-B-38-17967 (U.S. Pat. No. 3,226,422), JP-B-39-8512, JP-B-45-35287, JP-A-48-47476 (the term "JP-A" as used herein means an "unexamined published Japanese patent application"), JP-B-51-33888 and JP-B-60-36812 (U.S. Pat. Nos. 4,162,234 and 4,377,534). Thus, improvements in these processes have been attempted from various viewpoints.

However, the use of these catalysts in a fluidized bed reaction is accompanied by problems in that the resulting acrylonitrile yield is not always satisfactorily high; that it is difficult to prepare a catalyst with sufficient strength; and that certain expensive materials such as cobalt should be used as a catalytic component. Accordingly, improvement in these known processes from an industrial viewpoint has been desired.

Some processes regarding the preparation of a molybdenum/bismuth fluidized bed catalyst are known. For example, JP-B-37-8568 (U.S. Pat. No. 3,044,965) teaches a process comprising spray-drying an ammonium nitrate-containing slurry comprising molybdenum, bismuth and silica. JP-B-54-12913 discloses a process for the preparation of a molybdenum/bismuth-/iron/sodium/phosphorus catalyst of a highly restricted composition range. JP-B-57-49253 (U.S. Pat. No. 3,746,657) discloses a process wherein a silica sol is added stepwise to an aqueous suspension containing a heptamolybdate at a temperature lower than 66° C. and then phosphoric acid and other components such as bismuth, iron, cobalt and nickel are further added thereto. Further, JP-A-55-56839 (U.S. Pat. No. 4,264,476), JP-A-55-139839 (U.S. Pat. No. 4,290,922), JP-A-57-65329 and JP-A-57-75147 each disclose a process for the preparation of a molybdenum/bismuth hardwearing fluidized catalyst wherein the pH value and temperature of a slurry containing the catalytic components are adjusted to 1 or below and 60° C. or below, respectively. JP-A-55-13187 (U.S. Pat. No. 4,212,766) discloses a process comprising preliminarily forming molybdate(s) and/or tungstate(s) of Bi, Te, Sb, Sn, Cu or a mixture thereof in an aqueous slurry prior to combining the same with other elements. Furthermore, JP-A-57-12827 discloses a process wherein a slurry containing molybdenum/bismuth/ antimony is heated to 40° to 150° C. for at least 30 minutes.

As described in JP-B-48-43096 (U.S. Pat. No. 3,766,092), however, a molybdenum/bismuth catalyst which does not contain cobalt gives only a low acrylonitrile yield. Further, it is difficult to obtain a fluidized bed catalyst having a strength suitable for a fluidized bed reaction in this case.

SUMMARY OF THE INVENTION

An object of the present invention is to provide a process for the production of acrylonitrile at a high yield by the vapor phase catalytic ammoxidation of propylene in a fluidized bed reactor with the use of a multi-component fluidized bed catalyst comprising molybdenum/bismuth/iron/antimony/nickel/alkali metal(s) as the components which has a high catalytic activity and a high attrition resistance and which does not require an expensive cobalt catalytic component.

The process for the production of acrylonitrile according to the present invention which in a first aspect comprises using a fluidized bed catalyst wherein the fluidized bed catalyst has a catalytic composition satisfying the following empirical formula:

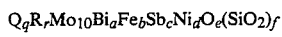

$$Q_qR_rMo_{10}Bi_aFe_bSb_cNi_dO_e(SiO_2)_f$$

wherein
Q represents P and/or B;
R represents at least one alkali metal element selected from the group consisting of Li, Na, K, Rb and Cs;
q, r, a, b, c, d, e and f each represent the atomic ratio of the element in the formula for which they are subscripts provided that
q is 0 to 3,
r is 0.01 to 1.5,
a is 0.1 to 3,
b is 0.1 to 2.5,
c is larger than 0 and not larger than 15 (when the Sb material is $Sb_2O_3$), larger than 0 and not larger than 30 (when the Sb material is $Sb_2O_4$) or larger than 0 and not larger than 8 (when the Sb material is $Sb_2O_5$),
d is 4 to 8,
e is the number of oxygen atoms corresponding to the oxides formed by combining the above components together, and
f is 20 to 150; and wherein the fluidized bed catalyst is produced by
(i) preparing a slurry containing the above catalytic components, with control of the pH value of the slurry to 5 or below; and
(ii) spray-drying the slurry containing the catalytic components obtained to thereby form spherical particles, and
(iii) calcining the spherical particles.

In a second aspect of the present invention, the preparation of the slurry containing the catalytic components described in the first aspect is carried out by:
(i) preparing a solution or a slurry containing at least the Mo and Fe components, of those catalyst components as described above, with control of the pH of the solution or slurry to 5 or below;
(ii) heating the solution or slurry obtained to 50° to 120° C. for at least ten minutes while maintaining the same in the form of a slurry;
(iii) adding the remaining catalytic components to the slurry at any stage before, during or after the step (ii);

(iv) spray-drying the slurry containing the catalytic components obtained to thereby form spherical particles; and (v) calcining the spherical particles.

BRIEF DESCRIPTION OF THE DRAWINGS

FIG. 1 is a scanning electron microscope photograph which shows the structure of a catalytic particle of the catalyst of the present invention obtained in Example 1, while

DETAILED DESCRIPTION OF THE INVENTION

Figure 1:
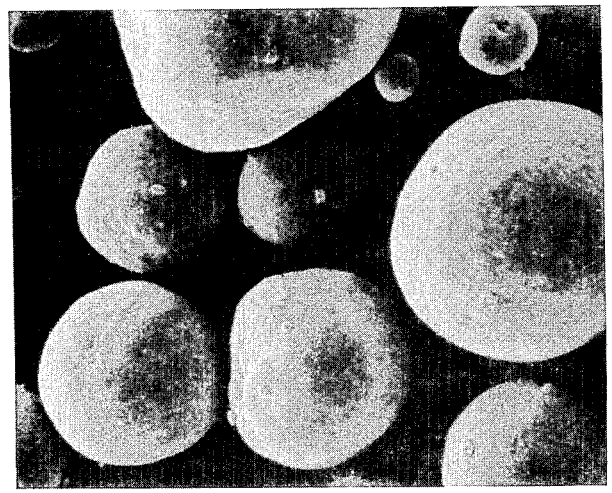
Figure 2:
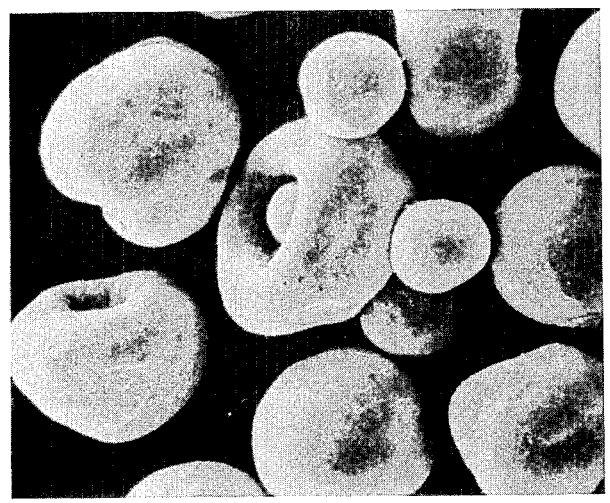
FIG. 2 is a scanning electron microscope photograph which shows that obtained in Comparative Example 1. The catalyst of the present invention has clearly a good shape, which provides a high attrition resitance.

The present invention is described in detail below.

The vapor phase catalytic ammoxidation of propylene in a fluidized bed is a known technique. Thus, it can be achieved in a known manner as described, for example, in U.S. Pat. Nos. 3,044,965 and 4,264,476 so long as it is compatible with the present invention.

The present invention comprises effecting the above-mentioned reaction in the presence of an oxide composition comprising molybdenum, bismuth, iron, antimony, nickel and alkali metal(s) each carried by silica, optionally together with additional components such as phosphorus or boron which are also carried by silica.

Importantly, in the present invention the catalyst to be used is selected. Any catalyst may be used therefor so long as it has a catalytic composition satisfying the above-mentioned empirical formula. In this catalytic composition, particularly preferable atomic ratios of the components in order to elevate the acrylonitrile yield are as follows: setting the Mo component at 10, q is 0.05 to 1.0, r is 0.05 to 1.0, a is 0.5 to 2.5, b is 0.5 to 2. c is 2 to 12 (when the Sb material is $Sb_2O_3$), 1 to 25 (when the Sb material is $Sb_2O_4$) or 0.5 to 7 (when the Sb material is $Sb_2O_5$), and f is 40 t 100.

At present, it is not completely clear how the catalytic components forming the catalyst of the present invention, namely, molybdenum, bismuth, iron, antimony, nickel, alkali metal(s), silicon, phosphorus and boron contribute to the expression of the activity and physical properties of said catalyst. However, the object of the present invention can be hardly achieved when the composition of the catalyst departs from the above empirical formula or when the conditions for the preparation of the catalyst are varied. These facts obviously indicate that these elements constituting the catalyst and the preparation conditions are closely related to the expression of the catalytic effects.

For example, a catalytic composition wherein q is larger than 3 (again where the amount of the Mo component is 10, the same will apply hereinafter), r is smaller than 0.01 or larger than 1.5, a is smaller than 0.1 or larger than 3, b is smaller than 0.1 or larger than 2.5, c is larger than 15 (when the Sb material is $Sb_2O_3$), larger than 30 (when the Sb material is $Sb_2O_4$) or larger than 8 (when the Sb material is $Sb_2O_5$) and d is smaller than 4 or larger than 8, gives a lowered acrylonitrile selectivity or poor catalytic properties. When f is smaller than 20, the strength of the catalyst is lowered. When f exceeds 150, on the other hand, the catalytic activity is lowered. When the nickel component is replaced by a cobalt component which belongs to the same group in the perioric table, acrylonitrile selectivity is lowered.

Another important aspect of the present invention resides in the production of the catalyst. Namely, the catalyst to be used in the present invention should be prepared by forming a slurry in the following manner.

Catalytic materials

As starting materials for the production of the catalyst to be used in the present invention, various materials such as the oxides, hydroxides, chlorides and nitrates can be used.

Examples of starting materials for the molybdenum component include molybdenum oxides such as molybdenum trioxides, molybdic acid, ammonium p-molybdate, ammonium m-molybdate and heteropolyacids containing molybdenum such as phosphomolybdic acid and silicomolybdic acid as well as their salts.

Examples of starting materials for the bismuth component include bismuth salts such as bismuth nitrate and bismuth sulfate, bismuth trioxide and metallic bismuth dissolved in nitric acid.

Examples of starting materials for the iron components include ferrous oxide, ferric oxide, ferrosoferric oxide, iron nitrate, iron chloride and iron hydroxide. Further, metallic iron heated and dissolved in nitric acid may be used therefor.

Examples of starting materials for the antimony component include antimony trioxide, antimony tetraoxide and antimony pentaoxide.

Examples of starting materials for the nickel component include nickel oxide, nickel hydroxide, nickel nitrate and metallic nickel dissolved in nitric acid.

Examples of starting materials for the phosphorus component represented by the component R include phosphoric acid and its salts such as ammonium phosphate or alkali metal phosphates. Examples of starting materials for the boron component represented by the component R include boric acid and its salts such as ammonium borate and alkali metal borates.

As starting materials for the component Q, namely, the alkali metal component, nitrates, carbonates, hydroxides, oxides and chlorides of alkali metals including lithium, sodium, potassium rubidium and cesium may be employed.

The catalyst to be used in the present invention employs silica as a carrier. This is because silica is markedly superior to other carriers in the strength of fluidized bed catalyst; it is almost inert to the catalytic components; and it exerts no undesirable effects on catalytic activity. Namely, the application of silica imparts a sufficient strength to the fluidized bed catalyst and an appropriate particle density for achieving an excellent fluidization as described, for example, in U.S. Pat. Nos. 3,044,965, 3,746,657 and 4,280,929.

Silica sol or a fine silica powder may be preferably used as the silica material, i.e., the carrier component. The silica sol preferably has a silica concentration of about 5 to 90% by weight.

Formation of slurry

In the formation of a slurry containing the catalytic components in a first aspect, the abovementioned Q, R, Mo, Bi, Fe, Ni, Sb and silica components are mixed together to thereby give an aqueous slurry. It is desirable that the slurry thus obtained is uniformly mixed.

Then, the pH value of this slurry is controlled to 5 or below, preferably 0.5 to 5, with stirring. When the pH value exceeds 5, the slurry becomes viscous or gels, which makes the stirring of the slurry difficult. Thus, a uniform slurry cannot be obtained in this case. Even if a slurry is formed tentatively, the viscosity thereof would immediately increase. Thus, the slurry cannot be spray-dried as such. When this slurry is diluted and spray-dried, the obtained catalyst has poor properties.

In the process of the present invention, heating the slurry is not always required. However, it is preferable that the slurry, whose pH value is thus controlled to 5 or lower, is heated to about 50° to 120° C., more preferably about 60° to 110° C., for at least about 10 minutes, most preferably about 0.5 to 8 hours, while maintaining the same in the form of a slurry. Thus, the slurry is further stabilized, which improves the catalytic effect of the final catalyst obtained.

When the slurry is to be heated as described above, the slurry should contain at least Mo and Fe components prior to the adjustment of the pH. That is to say, in a second aspect, the slurry may be prepared in the following manner. First the Mo and Fe components, among those catalytic materials described above, are mixed to thereby give a solution or a slurry, which will be simply called a slurry hereinafter, containing the same. Then, the pH of the slurry is controlled to 5 or below with thorough stirring. The Q, R, Bi, Ni, Sb and silica components may be either mixed initially or added to the slurry following the pH adjustment or heating.

It is not well understood at present what reaction occurs in the slurry during the heating process. However, an X-ray diffraction pattern of a catalyst prepared by heating the slurry differs from that of the pattern prepared without heating the same. This fact suggests that some reaction might proceed during the heating process. It is assumed that such a reaction would give an excellent catalytic activity and density the material slurry particles to thereby elevate the strength of the catalyst product. Further, the heated slurry becomes stable.

These pH-adjustment and heating steps are effective on a slurry containing both of the Mo and Fe components. When either one of these component is present alone in the slurry, the obtained catalyst does not exhibit excellent activity nor preferable physical properties.

Spray-drying

The slurry thus prepared is then formulated into fine spherical particles by spray-drying. The spray-drying may be carried out using conventional techniques. Namely, a conventional device such as pressure nozzle or rotating disc may be used therefor. The concentration of the slurry to be spray-deried preferably ranges from approximately 10 to 40% by weight, based on the oxides of the elements constituting the catalyst. Although this range is not critical, a concentration lower than the lower limit is economically disadvantageous while one exceeding the upper limit gives poor workability. The spray-drying should be carried out in a manner so as to produce particles of the desired particle size distribution by appropriately controlling the concentration of the slurry and the spray-drying conditions.

Calcination

The fine spherical particles obtained by the above spray-drying are then dried, if required, and calcined finally at a temperature of about 500° to 750° C. to produce a high activity and preferable physical properties. The calcination may be carried out either in two steps, i.e., provisional calcination and main calcination or calcination at a single temperature. It is preferable that the spherical particles obtained by the spray-drying are provisionally calcined at about 200° to 500° C. for about 1 to 50 hours and then finally calcined at about 500° to 750° C. for about 1 to 50 hours. The calcination is preferably carried out under nonreductive atmosphere which means the atmosphere of oxygen containing gases or inert gases such as steam, carbon oxides, nitrogen, etc. From an economical viewpoint, it may be preferably effected in an air stream. Various calcination devices such as tunnel oven, rotating oven or fluidized oven may be selected therefor.

For fluidized bed use, there way be preferably used about 10 to 150 microns in particle size.

The process using the catalyst of the present invention may be carried out in a fluidized bed catalytic reactor. Namely, it may be effected by feeding propylene, ammonia and oxygen to a reactor peaked with the fluidized bed catalyst of the present invention. As the oxygen source, air is preferable from an economical reason. The air may be appropriately enriched with oxygen, if desired.

The molar ratio of the oxygen/propylene in the feed gas may range from about 1:1 to about 4:1. Since the catalyst of the present invention has a high acrylonitrile selectivity, the molar ratio may be relatively low, i.e., from about 1.5:1 to about 2.5:1. The molar ratio of the ammonia/propylene in the feed gas may be adjusted within a range of about 0.8:1 to about 3:1, preferably about 0.9:1 to about 1.5:1. Further, inert gas(es) such as nitrogen or steam may be fed, if desired.

The reaction may be carried out at a temperature of about 380° to 500° C., preferably about 400° to 480° C. The reaction pressure may range from 0 to about 3 $kg/cm^2 \times G$. The apparent contact time may range from about 1 to 30 sec, preferably about 2 to 20 sec.

The catalyst of the first embodiment of the present invention containing molybdenum, bismuth, iron, antimony, nickel and alkali metal(s) has a high activity in the production of acrylonitrile from propylene, a high fluidization capability and a high mechanical strength. Thus, it is preferred as a fluidized bed catalyst. These catalytic properties of this catalyst are further elevated in the second embodiment of the present invention. Namely, the process of the present invention makes it possible to advantageously produce acrylonitrile by vapor phase catalytic ammoxidation of propylene in a fluidized bed on an industrial scale, compared with conventional methods.

To further illustrate the present invention, and not by way of limitation, the following Examples are given. Unless otherwise indicated, all parts, percents, ratios and the like are by weight.

In the following Examples, the catalytic activities were determined in the following manner.

A fluidized bed type reactor whose catalyst fluidized portion was 2.5 cm in internal diameter and 40 cm in height was packed with a catalyst. Then, a gas of the following composition was fed thereto. The reaction pressure was atmospheric.

Oxygen (fed as air)/Propylene=2.0:1 (mol/mol).
Ammonia/Propylene=1.2:1 (mol/mol).

The expressions "Acrylonitrile Yield" and "Propylene Conversion" used herein are defined as follows, respectively:

Acrylonitrile Yield (%) =

$$\frac{\text{Weight of Carbon in Acrylonitrile Formed}}{\text{Weight of Carbon in Propylene Fed}} \times 100$$

Propylene conversion (%) =

$$\frac{\text{Weight of Carbon in Propylene Consumed}}{\text{Weight of Carbon in Propylene Fed}} \times 100$$

The strength of the catalyst was evaluated in the following manner.

The method described in "Test Methods for Synthetic Cracking Catalysts" (American Cynamid Co., Ltd. 6/31-4m-1/57), which is a known collection of testing methods for catalysts used in fluid catalytic cracking, was used. The Attarition Loss (%) was determined according to the following equation:

Attrition Loss (%) = B × 100/(C-A)

wherein
A represents the weight of the catalyst worn within 0 to 50 hours;
B represents the weight of the catalyst worn within 5 to 20 hours; and
C represents the weight of the tested catalyst.

In this test, C was 50 (g). The higher the attrition resistance, the smaller the R value (%) that the catalyst showed.

EXAMPLE 1

A catalyst having an empirical formula: $K_{0.2}Mo_{12.0}Bi_{1.5}Fe_{1.5}Sb_4Ni_6O_{48.6}(SiO_2)_{50}$ was prepared by the following method.

2.70 g of potassium nitrate was dissolved in 27.0 ml of water. The solution obtained was added to 2008 g of 20% silica sol. To the resulting solution, was added 236 g of ammonium p-molybdate dissolved in 590 ml of water at 80° C. Subsequently, 78.7 g of antimony trioxide powder, 238 g of nickel nitrate dissolved in 240 ml of water, 81 g of iron nitrate dissolved in 80 ml of water and 99.2 g of bismuth nitrate dissolved in 99 ml of 10% nitrate were successively added. Then, the pH of the mixture obtained was adjusted 2.0 with 15% aqueous ammonia.

The slurry thus obtained was spray-dried with a rotating disc spray drier whose inlet and outlet temperatures were controlled to 320° C. and 160° C., respectively. The catalyst thus dried was heated at 250° C. and calcined at 400° C. for 2.5 hours and finally at 580° C. for three hours.

EXAMPLES 2 AND 3

The procedure of Example 1 was repeated to thereby to give catalysts of the composition of Examples 2 and 3 shown in Table 1 below.

EXAMPLE 4

Antimony trioxide was calcined in the atmosphere. The calcined product was identified as pure antimony tetraoxide by X-ray diffractometry. The procedure of Example 1 was repeated except that the antimony trioxide as used in Example 1 was replaced by 82.9 g of the ground antimony tetraoxide obtained above. Thus, a catalyst of the same composition as that described in Example 1 was obtained.

EXAMPLES 5 AND 6

The procedure of Example 4 was repeated thereby to give catalysts of the compositions of Examples 5 and 6 in Table 1 below.

EXAMPLE 7

Hydrated antimony pentaoxide was precipitated by hydrolyzing antimony pentachloride. The obtained precipitate was thoroughly filtered and washed until no chlorine ion was detected. This filter cake of hydrated antimony pentaoxide was suspended in water to thereby give an antimony pentaoxide slurry having an antimony pentaoxide concentration of 10% by weight. The procedure of Example 1 was repeated except that the antimony trioxide was replaced by 864.7 g of the antimony pentaoxide slurry obtained above. Thus, a catalyst of an empirical formula: $K_{0.2}Mo_{10}Bi_{1.5}Fe_{1.5}Sb_2Ni_6O_{44.6}(SiO_2)_{50}$ was obtained.

EXAMPLE 8

The procedure of Example 7 was repeated thereby to give a catalyst of the same composition at that described in Example 1.

EXAMPLES 9 to 18

The procedure of Example 4 was repeated thereby to give catalysts of the compositions of Examples 9 to 18 shown in Table 1 below.

EXAMPLE 19

The procedure of Example 4 was repeated except that 13.22 g of 85% orthophosphoric acid was added following the bismuth nitrate. Thus, a catalyst of an empirical formula: $P_{1.0}K_{0.2}Mo_{10}Bi_{1.5}Fe_{1.5}Sb_{10}Ni_6O_{61.1}(SiO_2)_{50}$ was obtained.

EXAMPLE 20

The procedure of Example 19 was repeated except that the orthophosphoric acid was replaced by 1.65 g of orthoboric acid. Thus, a catalyst of an empirical formula: $B_{0.2}K_{0.2}Mo_{10}Bi_{1.5}Fe_{1.5}Sb_{10}Ni_6O_{61.1}(SiO_2)_{50}$ was obtained.

EXAMPLE 21

The procedure of Example 4 was repeated except that the potassium nitrate was replaced by 1.30 g of cesium nitrate. Thus, a catalyst of an empirical formula: $Cs_{0.05}Mo_{10}Bi_{1.5}Fe_{1.5}Sb_{10}Ni_6O_{60.5}(SiO_2)_{50}$ was obtained.

EXAMPLE 22

The procedure of Example 4 was repeated except that the potassium nitrate was replaced by 1.97 g of rubidium nitrate. Thus, a catalyst of an empirical formula: $Rb_{0.1}Mo_{10}Bi_{1.5}Fe_{1.5}Sb_{10}Ni_6O_{60.6}(SiO_2)_{50}$ was obtained.

EXAMPLES 23 AND 24

The procedure of Example 4 was repeated except that the pH of the slurry was adjusted to 1 or 5. Thus, a catalyst of an empirical formula: $K_{0.2}Mo_{10}Bi_{1.5}Fe_{1.5}Sb_{10}Ni_6O_{60.5}(SiO_2)_{50}$ was obtained.

COMPARATIVE EXAMPLE 1

The procedure of Example 1 was repeated except that no antimony trioxide was added. Thus, a catalyst of an empirical formula: $K_{0.2}Mo_0Bi_{1.5}Fe_{1.5}Ni_6O_{40.6}(SiO_2)_{50}$ was obtained.

COMPARATIVE EXAMPLE 2

The procedure of Example 1 was repeated thereby to give a catalyst of the composition of Comparative Example 2 shown in Table 2 below.

COMPARATIVE EXAMPLE 3

The procedure of Example 4 was repeated thereby to give a catalyst of the composition of Comparative Example 3 shown in Table 2 below.

COMPARATIVE EXAMPLE 4

The procedure of Example 7 was repeated thereby to give a catalyst of the composition of Comparative Example 4 shown in Table 2 below.

COMPARATIVE EXAMPLES 5 to 14

The procedure of Example 4 was repeated thereby to give catalysts of the compositions of Comparative Examples 5 to 14 shown in Table 2 below.

COMPARATIVE EXAMPLE 15

The procedure of Example 5 was repeated thereby to give a slurry of a catalyst of the same composition. Then, the pH of the slurry obtained was adjusted to 5.5. As a result, the slurry viscosity became extremely high, which made spray-drying impossible.

COMPARATIVE EXAMPLE 16

The procedure of Example 4 was repeated except that the nickel nitrate was replaced by cobalt nitrate thereby to give a catalyst of an empirical formula: $K_{0.2}Mo_{10}Bi_{1.5}Sb_{10}Co_6O_{60.5}(SiO_2)_{50}$.

The activity and catalytic strength of each catalyst obtained in the Examples 1 to 24 and Comparative Examples 1 to 16 above were tested. The results obtained are shown in Table 1 (Examples) and Table 2 (Comparative Examples) below.

EXAMPLE 25

A catalyst having an empirical formula: $K_{0.2}Mo_{10}Bi_{1.5}Fe_{1.5}Sb_4Ni_6O_{48.6}(SiO_2)_{50}$ was prepared by the following method.

2.70 g of potassium nitrate was dissolved in 27.0 ml of water. The solution obtained was added to 2008 g of 20% silica sol. To the resulting solution, was added 236 g of ammonium p-molybdate dissolved in 590 ml of water at 80° C. Subsequently, 78.7 g of antimony trioxide powder, 238 g of nickel nitrate dissolved in 240 ml of water, 81 g of iron nitrate dissolved in 80 ml of water and 99.2 g of bismuth nitrate dissolved in 99 ml of 10% nitrate were successively added. Then, the pH of the mixture obtained was adjusted to 2.0 with 15% aqueous ammonia.

The uniform slurry thus obtained was introduced into a three-neck flask and heated under reflux at 100° C. for one hour with stirring.

After heating, the slurry was spray-dried with a rotating disc spray drier whose inlet and outlet temperatures were controlled to 320° C. and 160° C., respectively. The catalyst thus dried was heated at 250° C. and calcined at 400° C. for 2.5 hours and finally at 580° C. for three hours.

EXAMPLES 26 AND 27

The procedure of Example 25 was repeated thereby to give catalysts of the compositions of Examples 26 and 27 shown in Table 3 below.

EXAMPLE 28

Antimony trioxide was calcined in the atmosphere. The calcined product was identified as pure antimony tetraoxide by X-ray diffractometry. The procedure of Example 25 was repeated except that the antimony trioxide was replaced by 82.9 g of the ground antimony tetraoxide obtained above. Thus, a catalyst of the same composition as that described in Example 1 was obtained.

EXAMPLES 29 AND 30

The procedure of Example 28 was repeated thereby to give catalysts of the compositions of Examples 29 and 30 shown in Table 1 below.

EXAMPLE 31

Hydrated antimony pentaoxide was precipitated by hydrolyzing antimony pentachloride. The precipitate obtained was thoroughly filtered and washed until no chlorine ion was detected. This filter cake of hydrated antimony pentaoxide was suspended in water thereby to give an antimony pentaoxide slurry having an antimony pentaoxide concentration of 10% by weight. The procedure of Example 25 was repeated except that the antimony trioxide was replaced by 864.7 g of the antimony pentaoxide slurry obtained above. Thus, a catalyst of an empirical formula: $K_{0.2}Mo_{10}Bi_{1.5}Fe_{1.5}Ni_6Sb_2O_{44.6}(SiO_2)_{50}$ was obtained.

EXAMPLE 32

The procedure of Example 31 was repeated thereby to give a catalyst of the same composition as that described in Example 25.

EXAMPLES 33 to 42

The procedure of Example 28 was repeated thereby to give catalysts of the compositions of Examples 33 to 42 shown in Table 3 below.

EXAMPLE 43

The procedure of Example 28 was repeated except that 13.22 g of orthophosphoric acid was added following the bismuth nitrate. Thus, a catalyst of an empirical formula: $P_{1.0}K_{0.2}Mo_{10}Bi_{1.5}Fe_{1.5}Ni_6Sb_{10}O_{61.1}(SiO_2)_{50}$ was obtained.

EXAMPLE 44

The procedure of Example 43 was repeated except that the orthophosphoric acid was replaced by 1.65 g of orthoboric acid. Thus, a catalyst of an empirical formula: $B_{0.2}K_{0.2}Mo_{10}Bi_{1.5}Fe_{1.5}Ni_6Sb_{10}O_{61.1}(SiO_2)_{50}$ was obtained.

EXAMPLE 45

The procedure of Example 28 was repeated except that the potassium nitrate was replaced by 1.30 g of cesium nitrate. Thus, a catalyst of an empirical formula: $Cs_{0.05}Mo_{10}Bi_{1.5}Fe_{1.5}Ni_6Sb_{10}O_{60.5}(SiO_2)_{50}$ was obtained.

EXAMPLE 46

The procedure of Example 28 was repeated except that the potassium nitrate was replaced by 1.97 g of rubidium nitrate. Thus a catalyst of an empirical formula: $Rb_{0.1}Mo_{10}Bi_{1.5}Fe_{1.5}Ni_6Sb_{10}O_{60.6}(SiO_2)_{50}$ was obtained.

EXAMPLES 47 AND 48

The procedure of Example 29 was repeated except that the pH of the slurry was adjusted to 1 or 5. Thus, catalysts of the same composition as that of Example 29 were obtained.

EXAMPLES 49 AND 50

The procedure of Example 29 was repeated except that the heating temperature and heating period of the slurry were varied. Thus, catalysts of the same composition as that of Example 29 were obtained.

EXAMPLES 51 TO 55

The procedure of Example 29 was repeated except that an aqueous solution of potassium nitrate, an aqueous solution of bismuth nitrate in 10% nitric acid, an antimony tetraoxide powder or an aqueous solution of nickel nitrate or silica sol of pH 2.0 were added to the heated slurry. Thus, catalysts of the same composition as that described in Example 29 were obtained.

COMPARATIVE EXAMPLE 17

The procedure of Example 25 was repeated thereby to give a catalyst of an empirical formula: $K_{0.2}Mo_{10}Bi_{1.5}Fe_{1.5}Sb_{18}Ni_6O_{76.6}(SiO_2)_{50}$.

COMPARATIVE EXAMPLE 18

The procedure of Example 28 was repeated thereby to give a catalyst of an empirical formula: $K_{0.2}Mo_{10}Bi_{1.5}Fe_{1.5}Sb_{40}Ni_6O_{76.6}(SiO_2)_{50}$.

COMPARATIVE EXAMPLE 19

The procedure of Example 31 was repeated thereby to give a catalyst of an empirical formula: $K_{0.2}Mo_{10}Bi_{1.5}Fe_{1.5}Sb_{10}Ni_6O_{60.6}(SiO_2)_{50}$.

COMPARATIVE EXAMPLES 20 TO 29

The procedure of Example 28 was repeated thereby to give catalysts of the compositions of Comparative Examples 20 to 29 in Table 4 below.

COMPARATIVE EXAMPLE 30

The pH of an unheated slurry was adjusted to 5.5 in the same manner as the one described in Example 29. As a result, the viscosity of the slurry became extremely high, which made it impossible to spray-dry the slurry.

COMPARATIVE EXAMPLE 31

The procedure of Example 29 was repeated except that the aqueous solution of iron nitrate was added after the heating. Thus, a catalyst of the same composition as that described in Example 29 was obtained.

COMPARATIVE EXAMPLE 32

The procedure of Example 29 was repeated except that the aqueous solution of ammonium p-molybdate was added after the heating. Thus, a catalyst of the same composition as that described in Example 29 was obtained.

COMPARATIVE EXAMPLE 33

The procedure of Example 29 was repeated except that the nickel nitrate was replaced by cobalt nitrate. Thus, a catalyst of an empirical formula: $K_{0.2}Mo_{10}Bi_{1.5}Fe_{1.5}Sb_{10}Co_6O_{60.6}(SiO_2)_{50}$ was obtained.

The activity and strength of each catalyst obtained in Examples 25 to 55 and Comparative Examples 17 to 33 above were evaluated. The results obtained are shown in Table 3 (Examples) and Table 4 (Comparative Examples) below.

TABLE 1

| Example No. | Catalytic Composition (atm. ratio) | | | | | | | | Sb Material | pH of Slurry | Calcination Temp. (°C.) | Reaction Temp. (°C.) | Contact Time (sec) | Acrylonitrile Yield (%) | Propylene Conversion (%) | Bulk Density (g/ml) | Attrition Resistance (R value) |
|---|---|---|---|---|---|---|---|---|---|---|---|---|---|---|---|---|---|
| | Q | R | Mo | Bi | Fe | Sb | Ni | Si | | | | | | | | | |
| 1 | — | K 0.2 | 10 | 1.5 | 1.5 | 4 | 6 | 50 | $Sb_2O_3$ | 2 | 580 | 405 | 4.5 | 83.5 | 99.0 | 0.86 | 1.2 |
| 2 | — | " | " | " | " | 6 | " | " | " | " | 580 | 410 | 4.5 | 84.5 | 98.3 | 0.90 | 1.1 |
| 3 | — | " | " | " | " | 10 | " | " | " | " | 585 | 410 | 4.5 | 83.8 | 98.5 | 0.98 | 0.9 |
| 4 | — | " | " | " | " | 4 | " | " | $Sb_2O_4$ | " | 575 | 410 | 4.0 | 84.0 | 98.5 | 0.93 | 1.1 |
| 5 | — | " | " | " | " | 10 | " | " | " | " | 590 | 420 | 4.5 | 86.2 | 98.0 | 1.01 | 0.9 |
| 6 | — | " | " | " | " | 25 | " | " | " | " | 580 | 420 | 4.5 | 85.3 | 98.4 | 1.12 | 1.0 |
| 7 | — | " | " | " | " | 2 | " | " | $Sb_2O_5$ | " | 585 | 410 | 4.0 | 83.3 | 97.9 | 0.91 | 1.3 |
| 8 | — | " | " | " | " | 4 | " | " | " | " | 600 | 410 | 4.0 | 83.1 | 98.3 | 0.95 | 1.1 |
| 9 | — | 0.05 | " | " | " | 10 | " | " | $Sb_2O_4$ | " | 600 | 410 | 4.5 | 84.1 | 98.2 | 1.01 | 1.1 |
| 10 | — | 1.0 | " | " | " | " | " | " | " | " | 575 | 410 | 5.0 | 84.7 | 97.5 | 1.02 | 1.0 |
| 11 | — | 0.2 | " | 0.5 | " | " | " | " | " | " | 550 | 415 | 4.5 | 83.7 | 98.2 | 1.00 | 1.2 |
| 12 | — | " | " | 2.5 | " | " | " | " | " | " | 600 | 410 | 5.5 | 84.0 | 98.5 | 1.02 | 1.2 |
| 13 | — | " | " | 1.5 | 0.5 | " | " | " | " | " | 520 | 405 | 5.5 | 83.5 | 97.7 | 1.00 | 1.3 |
| 14 | — | " | " | " | 2.0 | " | " | " | " | " | 620 | 420 | 4.0 | 84.7 | 98.0 | 1.25 | 1.0 |
| 15 | — | " | " | " | 1.5 | " | 4.5 | " | " | " | 510 | 420 | 5.0 | 84.2 | 98.5 | 1.01 | 1.2 |
| 16 | — | " | " | " | " | " | 7.5 | " | " | " | 675 | 420 | 5.0 | 83.3 | 98.3 | 1.04 | 0.9 |
| 17 | — | K 0.2 | 1.0 | " | " | " | 6 | 40 | " | " | 530 | 405 | 3.5 | 85.1 | 98.7 | 1.03 | 1.4 |
| 18 | — | " | " | " | " | " | " | 80 | " | " | 660 | 430 | 6.0 | 84.5 | 97.0 | 0.92 | 0.9 |
| 19 | P 1.0 | " | " | " | " | " | " | 50 | " | " | 580 | 410 | 5.0 | 85.5 | 98.8 | 1.01 | 1.2 |
| 20 | B 0.2 | " | " | " | " | " | " | " | " | " | 580 | 410 | 5.0 | 86.0 | 98.7 | 1.01 | 1.2 |
| 21 | — | Cs 0.05 | " | " | " | " | " | " | " | " | 575 | 410 | 4.0 | 84.7 | 98.5 | 1.01 | 1.2 |
| 22 | — | Rb 0.1 | " | " | " | " | " | " | " | " | 580 | 410 | 4.5 | 86.1 | 98.6 | 1.01 | 1.1 |

TABLE 1-continued

| Example No. | Catalytic Composition (atm. ratio) | | | | | | | | Sb Material | pH of Slurry | Calcination Temp. (°C.) | Reaction Temp. (°C.) | Contact Time (sec) | Acrylonitrile Yield (%) | Propylene Conversion (%) | Bulk Density (g/ml) | Attrition Resistance (R value) |
|---|---|---|---|---|---|---|---|---|---|---|---|---|---|---|---|---|---|
| | Q | R | Mo | Bi | Fe | Sb | Ni | Si | | | | | | | | | |
| | | K | | | | | | | | | | | | | | | |
| 23 | — | 0.2 | " | " | " | " | " | " | " | 1 | 575 | 410 | 4.0 | 85.9 | 98.0 | 1.02 | 1.2 |
| 24 | — | " | " | " | " | " | " | " | " | 5 | 610 | 410 | 4.5 | 86.1 | 98.5 | 1.00 | 1.2 |

TABLE 2

| Comparative Example No. | Catalytic Composition (atm. ratio) | | | | | | | | Sb Material | pH of Slurry | Calcination Temp. (°C.) | Reaction Temp. (°C.) | Contact Time (sec) | Acrylonitrile Yield (%) | Propylene Conversion (%) | Bulk Density (g/ml) | Attrition Resistance (R value) |
|---|---|---|---|---|---|---|---|---|---|---|---|---|---|---|---|---|---|
| | Q | R | Mo | Bi | Fe | Sb | Ni | Si | | | | | | | | | |
| | | K | | | | | | | | | | | | | | | |
| 1 | — | 0.2 | 10 | 1.5 | 1.5 | — | 6 | 50 | — | 2 | 575 | 410 | 4.5 | 82.5 | 98.7 | 0.85 | 5.0 |
| 2 | — | " | " | " | " | 18 | " | " | $Sb_2O_3$ | " | 500 | 410 | 7.0 | 73.5 | 94.5 | 1.10 | 1.2 |
| 3 | — | " | " | " | " | 40 | " | " | $Sb_2O_4$ | " | 570 | 410 | 6.0 | 82.7 | 96.0 | 1.23 | 1.3 |
| 4 | — | " | " | " | " | 10 | " | " | $Sb_2O_5$ | " | 625 | 410 | 6.0 | 64.5 | 90.4 | 0.94 | 1.2 |
| 5 | — | — | " | " | " | " | " | " | $Sb_2O_4$ | " | 600 | 430 | 4.5 | 80.3 | 97.5 | 1.02 | 1.3 |
| 6 | — | 2.0 | " | " | " | " | " | " | " | " | 550 | 410 | 6.0 | 80.5 | 98.0 | 1.03 | 1.2 |
| 7 | — | 0.2 | " | — | " | " | " | " | " | " | 525 | 410 | 5.0 | 71.0 | 96.7 | 1.01 | 1.2 |
| 8 | — | " | " | 3.5 | " | " | " | " | " | " | 600 | 410 | 6.0 | 79.2 | 98.5 | 1.05 | 1.2 |
| 9 | — | " | " | 1.5 | — | " | " | " | " | " | 525 | 410 | 7.0 | 58.0 | 88.3 | 1.03 | 6.7 |
| 10 | — | " | " | " | 3 | " | " | " | " | " | 650 | 410 | 5.5 | 80.5 | 98.1 | 1.03 | 1.2 |
| 11 | — | " | " | " | 1.5 | " | 3.5 | " | " | " | 505 | 420 | 4.5 | 80.4 | 96.4 | 1.00 | 1.0 |
| 12 | — | " | " | " | " | " | 8.5 | " | " | " | 680 | 420 | 6.5 | 80.4 | 98.6 | 1.03 | 1.2 |
| 13 | — | " | " | " | " | " | 6 | 15 | " | " | 500 | 400 | 3.0 | 83.5 | 97.2 | 1.10 | 8.2 |
| 14 | — | " | " | " | " | " | " | 200 | " | " | 680 | 450 | 7.0 | 76.3 | 84.0 | 0.83 | 1.0 |
| 15 | — | " | " | " | " | " | " | 50 | " | 5.5 | Slurry set to gel at pH adjustment. | | | | | | |
| 16 | — | " | " | " | " | " | Co 6 | " | " | 2 | 550 | 410 | 6.0 | 81.8 | 97.0 | 0.90 | 1.1 |

TABLE 3

| Example No. | Catalytic Composition (atm. ratio) | | | | | | | | Sb Material | pH of Unheated Slurry | Heating Temp. (°C.) | Heating Period (hr) |
|---|---|---|---|---|---|---|---|---|---|---|---|---|
| | Q | R | Mo | Bi | Fe | Sb | Ni | Si | | | | |
| | | K | | | | | | | | | | |
| 25 | — | 0.2 | 10 | 1.5 | 1.5 | 4 | 6 | 50 | $Sb_2O_3$ | 2 | 100 | 1 |
| 26 | — | " | " | " | " | 6 | " | " | " | " | " | " |
| 27 | — | " | " | " | " | 10 | " | " | " | " | " | " |
| 28 | — | " | " | " | " | 4 | " | " | $Sb_2O_4$ | " | " | " |
| 29 | — | " | " | " | " | 10 | " | " | " | " | " | " |
| 30 | — | " | " | " | " | 25 | " | " | " | " | " | " |
| 31 | — | " | " | " | " | 2 | " | " | $Sb_2O_5$ | " | " | " |
| 32 | — | " | " | " | " | 4 | " | " | " | " | " | " |
| 33 | — | 0.05 | " | " | " | 10 | " | " | $Sb_2O_4$ | " | " | " |
| 34 | — | 1.0 | " | " | " | " | " | " | " | " | " | " |
| 35 | — | 0.2 | " | 0.5 | " | " | " | " | " | " | " | " |
| 36 | — | " | " | 2.5 | " | " | " | " | " | " | " | " |
| | | K | | | | | | | | | | |
| 37 | — | 0.2 | " | 1.5 | 0.5 | " | " | " | " | " | " | " |
| 38 | — | " | " | " | 2.0 | " | " | " | " | " | " | " |
| 39 | — | " | " | " | 1.5 | " | 4.5 | " | " | " | " | " |
| 40 | — | " | " | " | " | " | 7.5 | " | " | " | " | " |
| 41 | — | " | " | " | " | " | " | 40 | " | " | " | " |
| 42 | — | " | " | " | " | " | " | 80 | " | " | " | " |
| | P | | | | | | | | | | | |
| 43 | 1.0 | " | " | " | " | " | " | 50 | " | " | " | " |
| | B | | | | | | | | | | | |
| 44 | 0.2 | " | " | " | " | " | " | " | " | " | " | " |
| | | Cs | | | | | | | | | | |
| 45 | — | 0.05 | " | " | " | " | " | " | " | " | " | " |
| | | Rb | | | | | | | | | | |
| 46 | — | 0.1 | " | " | " | " | " | " | " | " | " | " |
| | B | K | | | | | | | | | | |
| 47 | 0.2 | 0.2 | " | " | " | " | 6 | " | " | 1 | " | " |
| 48 | — | " | " | " | " | " | " | " | " | 5 | " | " |
| 49 | — | " | " | " | " | " | " | " | " | 2 | " | 8 |
| 50 | — | " | " | " | " | " | " | " | " | " | 60 | " |
| 51 | — | " | " | " | " | " | " | " | " | " | 100 | 1 |
| 52 | — | " | " | " | " | " | " | " | " | " | " | " |
| 53 | — | " | " | " | " | " | " | " | " | " | " | " |
| 54 | — | " | " | " | " | " | " | " | " | " | " | " |

TABLE 3-continued

| Example No. | Additive after Heating | Calcination Temp. (°C.) | Reaction Temp. (°C.) | Contact Time (sec) | Acrylonitrile Yield (%) | Propylene Conversion (%) | Bulk Density (g/ml) | Attrition Resistance (R value) |
|---|---|---|---|---|---|---|---|---|
| 55 | — | " | " | " | " | " | " | " | " |
| 25 | — | 580 | 405 | 4.5 | 83.7 | 98.8 | 0.97 | 0.7 |
| 26 | — | 580 | 410 | 4.5 | 84.8 | 98.5 | 1.00 | 0.6 |
| 27 | — | 585 | 410 | 4.5 | 84.0 | 98.3 | 1.07 | 0.4 |
| 28 | — | 575 | 410 | 4.0 | 84.2 | 98.7 | 1.03 | 0.6 |
| 29 | — | 590 | 420 | 4.5 | 86.5 | 98.5 | 1.12 | 0.4 |
| 30 | — | 580 | 420 | 4.5 | 85.7 | 98.4 | 1.21 | 0.5 |
| 31 | — | 585 | 410 | 4.0 | 83.5 | 98.0 | 1.00 | 0.8 |
| 32 | — | 600 | 410 | 4.0 | 83.3 | 98.5 | 1.03 | 0.6 |
| 33 | — | 600 | 410 | 4.5 | 84.5 | 98.3 | 1.11 | 0.6 |
| 34 | — | 575 | 410 | 5.0 | 84.7 | 97.3 | 1.12 | 0.7 |
| 35 | — | 550 | 415 | 4.5 | 83.9 | 98.5 | 1.10 | 0.7 |
| 36 | — | 600 | 410 | 5.5 | 84.0 | 98.3 | 1.12 | 0.7 |
| 37 | — | 520 | 405 | 5.5 | 83.7 | 98.0 | 1.10 | 0.8 |
| 38 | — | 620 | 420 | 4.0 | 84.8 | 98.1 | 1.15 | 0.5 |
| 39 | — | 510 | 420 | 5.0 | 84.3 | 98.7 | 1.11 | 0.7 |
| 40 | — | 675 | 420 | 5.0 | 83.4 | 98.5 | 1.14 | 0.4 |
| 41 | — | 530 | 405 | 3.5 | 85.5 | 98.8 | 1.12 | 0.9 |
| 42 | — | 660 | 430 | 6.0 | 84.9 | 98.0 | 1.01 | 0.4 |
| 43 | — | 580 | 410 | 5.0 | 85.9 | 98.7 | 1.10 | 0.7 |
| 44 | — | 580 | 410 | 5.0 | 86.2 | 98.5 | 1.10 | 0.7 |
| 45 | — | 575 | 410 | 4.0 | 85.0 | 98.5 | 1.11 | 0.7 |
| 46 | — | 580 | 410 | 4.5 | 86.1 | 98.5 | 1.10 | 0.6 |
| 47 | — | 575 | 410 | 4.0 | 85.9 | 98.0 | 1.11 | 0.7 |
| 48 | — | 610 | 410 | 4.5 | 86.1 | 98.5 | 1.12 | 0.7 |
| 49 | — | 585 | 410 | 5.0 | 85.3 | 98.7 | 1.05 | 0.8 |
| 50 | — | 580 | 410 | 4.5 | 85.7 | 98.5 | 1.08 | 0.6 |
| 51 | K | 585 | 410 | 5.5 | 86.5 | 98.8 | 1.12 | 0.7 |
| 52 | Bi | 590 | 410 | 5.0 | 86.0 | 98.5 | 1.10 | 0.7 |
| 53 | Sb | 580 | 410 | 4.5 | 86.6 | 98.5 | 1.13 | 0.6 |
| 54 | Ni | 600 | 410 | 5.0 | 86.2 | 98.4 | 1.01 | 0.6 |
| 55 | Si | 600 | 415 | 4.5 | 86.3 | 98.5 | 1.04 | 0.7 |

TABLE 4

| Comparative Example No. | Catalytic Composition (atm. ratio) | | | | | | | Sb Material | pH of Unheated Slurry | Heating Temp. (°C.) | Heating Period (hr) |
|---|---|---|---|---|---|---|---|---|---|---|---|
| | Q | R | Mo | Bi | Fe | Sb | Ni | Si | | | | |
| | | K | | | | | | | | | | |
| 17 | — | 0.2 | 10 | 1.5 | 1.5 | 18 | 6 | 50 | Sb$_2$O$_3$ | 2 | 100 | 1 |
| 18 | — | " | " | " | " | 40 | " | " | Sb$_2$O$_4$ | " | " | " |
| 19 | — | " | " | " | " | 10 | " | " | Sb$_2$O$_5$ | " | " | " |
| 20 | — | — | " | " | " | " | " | " | Sb$_2$O$_4$ | " | " | " |
| 21 | — | 2.0 | " | " | " | " | " | " | " | " | " | " |
| 22 | — | 0.2 | " | — | " | " | " | " | " | " | " | " |
| 23 | " | " | " | 3.5 | " | " | " | " | " | " | " | " |
| 24 | — | " | " | 1.5 | — | " | " | " | " | " | " | " |
| 25 | — | " | " | " | 3.5 | " | " | " | " | " | " | " |
| 26 | — | " | " | " | 1.5 | " | 3.5 | " | " | " | " | " |
| 27 | — | " | " | " | " | " | 8.5 | " | " | " | " | " |
| | | K | | | | | | | | | | |
| 28 | — | 0.2 | " | " | " | " | 6 | 15 | " | " | " | " |
| 29 | — | " | " | " | " | " | " | 200 | " | " | " | " |
| 30 | — | " | " | " | " | " | " | 50 | " | 5.5 | " | " |
| 31 | — | " | " | " | " | " | " | " | " | 2.0 | " | " |
| 32 | — | " | " | " | " | " | " | " | " | " | " | " |
| | | | | | | | Co | | | | | |
| 33 | — | " | " | " | " | " | 6 | " | " | " | " | " |

| Comparative Example No. | Additive after Heating | Calcination Temp. (°C.) | Reaction Temp. (°C.) | Contact Time (sec) | Acrylonitrile Yield (%) | Propylene Conversion (%) | Bulk Density (g/ml) | Attrition Resistance (R value) |
|---|---|---|---|---|---|---|---|---|
| 17 | — | 500 | 410 | 7.0 | 74.0 | 94.7 | 1.15 | 0.7 |
| 18 | — | 570 | 410 | 6.0 | 82.3 | 96.5 | 1.25 | 0.8 |
| 19 | — | 625 | 410 | 6.0 | 65.0 | 91.0 | 1.05 | 0.7 |
| 20 | — | 600 | 420 | 4.5 | 80.5 | 98.1 | 1.11 | 0.8 |
| 21 | — | 550 | 410 | 6.0 | 80.7 | 98.2 | 1.12 | 0.7 |
| 22 | — | 525 | 410 | 5.0 | 71.5 | 97.0 | 1.10 | 0.7 |
| 23 | — | 600 | 410 | 6.0 | 79.3 | 98.6 | 1.14 | 0.7 |
| 24 | — | 525 | 410 | 7.0 | 59.0 | 89.5 | 1.12 | 3.4 |

TABLE 4-continued

| | | | | | | | | |
|---|---|---|---|---|---|---|---|---|
| 25 | — | 650 | 410 | 5.5 | 80.6 | 98.4 | 1.12 | 0.7 |
| 26 | — | 505 | 420 | 4.5 | 80.6 | 96.5 | 1.10 | 0.6 |
| 27 | — | 680 | 420 | 6.5 | 80.5 | 98.7 | 1.12 | 0.7 |
| 28 | — | 500 | 400 | 3.0 | 83.6 | 97.5 | 1.25 | 7.6 |
| 29 | — | 680 | 450 | 7.0 | 76.5 | 85.0 | 0.92 | 0.5 |
| 30 | — | Slurry set to gel at pH-adjustment. | | | | | | |
| 31 | Fe | 575 | 410 | 4.5 | 82.3 | 98.2 | 0.96 | 4.0 |
| 32 | Mo | 575 | 410 | 6.0 | 74.8 | 96.7 | 1.01 | 0.7 |
| 33 | — | 550 | 410 | 6.0 | 81.2 | 97.5 | 1.01 | 0.6 |

From the comparison between Table 1 and Table 2 and the comparison between Table 3 and Table 4, the following facts can be seen.

(1) The catalysts of the present invention as shown in Tables 1 and 3 give a good acrylonitrile yield.

(2) The suitable ranges of the Sb component in a catalytic compositon of the present invention vary according to a strting material for the Sb component (see Examples 1 to 8 and 25 to 32). When the Sb component are not within the ranges of the present invention, the acrylonitrile yield is reduced (see Comparative Examples 1 to 4 and 17 to 19).

(3) When the pH of the slurry is 5 or below, a uniform slurry can be obtained thereby to easily produce a catalyst, whereas it is difficult to spray-dry the slurry with the pH of 5.5 because of its gelation (see Comparative Examples 15 to 30).

(4) When the nickel component in a catalytic composition of the present invention is replaced by a cobalt component which belongs to the same group in the perioric table, the acrylonitrile yield is reduced (see Comparative Examples 16 and 33).

(5) When the Mo component and Fe component are added after heating a slurry, the acrylonitrile yield is reduced (Comparative Examples 31 and 32).

While the invention has been described in detail and with reference to specific embodiments thereof, it will be apparent to one skilled in the art that various changes and modifications can be made therein without departing from the spirit and scope thereof.

What is claimed is:

1. A process for the production of acrylonitrile by the vapor phase catalytic ammoxidation of propylene in a fluidized bed using a fluidized bed catalyst, wherein the fluidized bed catalyst has a catalytic composition satisfying the following empirical formula:

$Q_qR_rMo_{10}Bi_aFe_bSb_cNi_dO_e(SiO_2)_f$ wherein

Q represents P and/or B;

R represents at least one alkali metal element selected from the group consisting of Li, Na, K, Rb and Cs;

q, r, a, b, c, d, e and f each represent the atomic ratio of the element in the formula for which they are subscripts provided that q is 0 to 3, r is 0.01 to 1.5, a is 0.1 to 3, b is 0.1 to 2.5, c is at least 2 and not larger than 15 (when the Sb material is $Sb_2O_3$), at least 2 and not larger than 30 (when the Sb material is $Sb_2O_4$) or at least 2 and not larger than 8 (when the Sb material is $Sb_2O_5$), d is 4 to 8, e is the number of oxygen atoms corresponding to the oxides formed by combining the above components together, and f is 20 to 150; and wherein the fluidized bed catalyst is produced by (i) preparing a slurry containing the above catalytic components, with control of the pH of said slurry to 5 or below;

(ii) spray-drying the slurry containing the catalytic components obtained to thereby form spherical particles, and (iii) calcining the spherical particles.

2. The process for the production of acrylonitrile of claim 1, wherein said process comprises (i) preparing a solution or a slurry containing at least the Mo and Fe components of those catalyst components as described in claim 1, with control of the pH of said solution or slurry to 5 or below;

(ii) heating the solution or slurry obtained to 50° to 120° C. while maintaining the same in the form of a solution or a slurry for at least ten minutes;

(iii) adding catalytic components as described in claim 1 other than the Mo and Fe components at any stage before, during or after the step (ii); (iv)-spray-drying the slurry containing the catalytic components obtained to thereby form spherical particles, and (v) calcining the spherical particles.

3. The process for the production of acrylonitrile of claim 1, wherein q is 0.05 to 1.0 r is 0.05 to 1.0 a is 0.5 to 2.5 b is 0.5 to 2 c is 2 to 12 when the Sb material is $Sb_2O_3$, 2 to 25 when the Sb material is $Sb_2O_4$, or 2 to 7 when the Sb material is $Sb_2O_5$, and f is 40 to 100.

4. The process for the production of acrylonitrile of claim 1, wherein the pH in step (i) is about 0.5 to 5.

5. The process for the production of acrylonitrile of claim 2, wherein the heating in step (ii) is to about 60° to 110° C.

6. The process for the production of acrylonitrile of claim 2, wherein the period of the heating in step (ii) is about 0.5 to 8 hours.

7. The process for the production of acrylonitrile of claim 1, wherein the calcining is at a temperature of about 500° to 750° C.

8. The process for the production of acrylonitrile of claim 1, wherein the calcining is conducted first by calcining at about 200° to 500° C. for about 1 to 50 hours and then by calcining at about 500° to 750° C. for about 1 to 50 hours.

* * * * *